(12) United States Patent
Levene et al.

(10) Patent No.: US 12,174,099 B2
(45) Date of Patent: Dec. 24, 2024

(54) TISSUE CHAMBER

(71) Applicant: APPLIKATE TECHNOLOGIES, INC., Washington, DC (US)

(72) Inventors: Michael Levene, Washington, DC (US); Richard Torres, East Haven, CT (US)

(73) Assignee: Applikate Technologies, Inc., Washington, DC (US)

( * ) Notice: Subject to any disclaimer, the term of this patent is extended or adjusted under 35 U.S.C. 154(b) by 0 days.

(21) Appl. No.: 18/154,447

(22) Filed: Jan. 13, 2023

(65) Prior Publication Data
US 2023/0204474 A1  Jun. 29, 2023

Related U.S. Application Data

(63) Continuation of application No. 16/735,061, filed on Jan. 6, 2020, now Pat. No. 11,555,765, which is a continuation of application No. 16/164,343, filed on Oct. 18, 2018, now Pat. No. 10,527,528.

(60) Provisional application No. 62/674,911, filed on May 22, 2018.

(51) Int. Cl.
| | |
|---|---|
| *G01N 1/00* | (2006.01) |
| *C12M 1/12* | (2006.01) |
| *G01N 1/30* | (2006.01) |
| *G01N 1/36* | (2006.01) |
| *G06T 7/00* | (2017.01) |

(52) U.S. Cl.
CPC ............... *G01N 1/36* (2013.01); *C12M 23/04* (2013.01); *C12M 25/06* (2013.01); *G01N 1/30* (2013.01); *G06T 7/0012* (2013.01); *G01N 2001/302* (2013.01); *G01N 2001/305* (2013.01)

(58) Field of Classification Search
None
See application file for complete search history.

(56) References Cited

U.S. PATENT DOCUMENTS

| | | | |
|---|---|---|---|
| 6,330,106 B1 | 12/2001 | Greenwald et al. | |
| 6,411,434 B1 | 6/2002 | Eastman et al. | |
| 7,179,424 B2 | 2/2007 | Williamson et al. | |
| 8,383,067 B2 * | 2/2013 | Williamson, IV | ....... G01N 1/31 435/40.5 |
| 10,495,554 B2 | 12/2019 | Deisseroth et al. | |

FOREIGN PATENT DOCUMENTS

WO   WO2007/079197   *   7/2007

* cited by examiner

*Primary Examiner* — Jyoti Nagpaul
(74) *Attorney, Agent, or Firm* — Sullivan & Worcester LLP; Thomas C. Meyers

(57) ABSTRACT

The present invention relates to systems and methods for tissue processing and analysis. Tissue chambers are configured to allow single-container chemical processing, imaging, and wax embedding of tissue samples in a single container without manipulation between steps. Tissue chambers with features to support the tissue sample and allow fluid flow between the tissue sample and the tissue chamber surface are disclosed. The features may be index matched to sample structures of interest or dissolvable in clearing solution to allow for in-chamber imaging with minimal distortion. Specialized tissue processing and wax removal apparatuses are also disclosed including for use with tissue chambers having frangible portions to permit ease of wax removal.

19 Claims, 10 Drawing Sheets

TISSUE CHAMBER

FIELD OF THE INVENTION

The present disclosure relates generally to histological systems and methods for simplified positioning, chemical processing, and/or imaging of tissue samples including imaging, staining, fixing, wax embedding, and wax removal in a single chamber.

BACKGROUND

Histology and histopathology involve the study of cells and tissues under a microscope to diagnose and monitor diseases, such as cancer. Many of the fundamental techniques involved in histological analysis are a century or more old and histological analysis is primarily performed by trained medical professionals.

For standard histological methods, such as creating a digital histological image, current steps include placing a tissue sample inside a plastic cassette with perforated walls that allow fluid access and exposing the cassette to a fluid environment that changes composition over time to provide chemical fixation of the tissue. The tissue is eventually dehydrated and permeated with wax before removing the wax-embedded specimen from the cassette by melting the wax. For each of the processing steps, the tissue sample is generally resting on the floor and/or wall of a plastic cassette providing poor fluid access to those portions of the sample without agitation.

After the wax permeation and removal, the specimen is re-positioned in molten wax and allowed to cool again to fix the specimen in an orientation that permits sectioning slices of the specimen in a plane of choice, optimized for clinical interpretation. The slices are then placed on a slide, stained, and then either viewed directly by a pathologist or presented to an imager for digitization.

The above approach requires manipulation of tissue during processing, incurring labor costs and significant processing time. Furthermore, small specimens including small skin biopsies and biopsies from the gastrointestinal tract where orientation is critically relevant may rotate and bend freely while the cassette is submerged in fluid and exposed to agitation or flow. Those specimens can therefore require significant manipulation and processing time for histological analysis.

Additionally, the full suite of processing steps described above must be completed before a pathologist can begin substantive analysis of the specimen thereby incurring labor costs and delaying diagnoses.

SUMMARY

The present invention provides a single chamber solution for sample processing (e.g., dehydration, fixation, staining, and wax embedding) thereby reducing costs, labor, and time required for histological analysis. Furthermore, the present invention allows for the efficient incorporation of intermediary imaging steps during tissue processing thereby offering benefits such as earlier access to diagnostic information and the potential to avoid the costly steps of manual cutting, staining, and slide distribution where the need for such activities can be ruled out based on initial imaging results.

Single chamber solutions provided herein allow a user to initially orient a sample within the chamber in the desired position for imaging and/or sectioning and then perform all sample processing including fixation and/or dehydration, initial dyeing, imaging, and eventual wax embedding without having to touch or otherwise manipulate the sample again. Accordingly, tissue chambers of the invention allow for automatic sample processing using various processing devices described herein. Container aspects such as features on the container surface to allow for fluid access, exchange, and/or flow to all sides of the sample, allow for the sample to be successfully processed (e.g., dehydrated, fixed, stained, cleared, and wax embedded) without the need for agitation or manipulation of the sample. Sealable ports, such as "self-sealing" syringe injection ports, permit fluid exposure, motion, and exchange while preventing potential air-bubble formation and trapping that could affect imaging. Index matched or solvent-susceptible features allow for initial sample imaging through the features without significant distortion. Additionally, inclusion of a substantially non-fluorescent and non-reflective sponge for mounting and/or positioning helps ensure position is maintained, prevents artifacts of tissue compression, allows fluid flow around specimen, and provides a surface for improved 'wetting'. When adequately index matched and optically transmissive, it can also allow imaging through more than one surface, of particular value for use of the multiphoton modality known as second harmonic generation.

Alternatives have been explored for fixing the position of small specimens during tissue processing so that re-positioning at the wax-embedding step is not necessary such as the techniques described in U.S. Pat. No. 8,796,038 and US 20080227144, incorporated herein by reference. However, none of those prior methods allow for imaging after the clearing step, will typically not work for orienting all types of biopsies including gastrointestinal or skin biopsy specimens, and still need eventual removal by manual cutting and staining prior to visual interpretation or digital scanning.

The present invention provides a significant advantage over existing techniques by allowing a specimen to be placed in a container for histologic analysis before chemical processing (e.g., fixation, or exposure to a dehydration solution) and to undergo chemical processing in the oriented position in a single container device that can be used for all the steps of dehydration, staining, clearing, and imaging. Furthermore, tissue chambers of the invention can then be used for wax-embedding and automated or machine-assisted removal of the wax-embedded sample using a wax removal device configured to work with tissue chambers of the invention.

Single-chamber processing as described herein can provide the additional advantage of minimizing reagent use. As noted, tissue chambers can include features operable to minimize the contact area between the floor and/or walls of the chamber and the sample, thereby permitting good fluid access to all areas of the sample for fixatives, stains, dehydration solutions, wax, and/or other processing fluids. The walls of the chamber as well as the features can be optically clear and/or refractive index matched to the clearing solution and/or the structures of the sample to be examined (e.g., organelles or proteins). In certain embodiments, the features may comprise a material that dissolves in the presence of certain solutions used in sample processing (e.g., a clearing solution) such that the features space the sample from the vessel walls and provide good fluid contact to all portions of the sample for processing but have dissolved before any initial imaging of the sample within the chamber and therefore do not disrupt the imaging process. The walls of the tissue chamber itself (or imaging window portions therein) are substantially optically clear and/or index matched to the clearing solution and/or the structures of the sample to be examined in preferred embodiments.

Processing of the sample within the chamber in a fixed position for imaging allows for tight control over the volume of the chamber and the reagents used in processing. Instead of placing a cassette containing tissue that is open to a fluid environment that may be hundreds of times the volume of the tissue as in prior techniques, a single sample processing vessel as described herein can have minimal dead-volume, reducing expenditure on reagents. Reagent conservation is particularly important for controlling dye costs, which could otherwise be prohibitive, particularly for fluorescent markers. Hence, a sample-tailored reagent vessel is particularly suited for processing that incorporates dyeing of un-embedded specimens, and especially fluorescent dyeing where the cost of the dye may be the largest cost-component.

The single chamber techniques described herein also reduce processing times over existing methods. With current methods, it is more economical to wait until sufficient samples have been received and "grossed" (placed into cassettes) before loading a tissue processor. The single chamber approach can be combined with a specialized tissue processor operable to receive tissue chambers of the present disclosure through, for example, interfacing with fluid inlet/outlets of the chamber. Once a chamber is loaded with a specimen, the specimen can be plugged in and processed immediately; reducing the time the specimen must sit idle waiting for additional samples as in multiplex processing. The same applies to the steps subsequent to embedding including slide collation, slide staining, and organization and scanning of slides for digitization.

As noted above, single chamber systems described herein allow for varying geometries to more tightly correspond to individual sample geometry, reducing chamber dead volume and reagent consumption. Chambers can be designed so that the sample is matched to the minimum-size vessel accommodating the specimen. For example, a long core biopsy can be placed in a long thin channel. In certain embodiments, the chamber has a geometry that is approximately that of a thick common microscope slide, with dimensions of approximately 2.5 mm×75 mm×10 mm.

Vessels can be coded (e.g., with a machine-readable symbol such as a matrix barcode (QR) or UPC code, or any symbol of recognizable shape, color, or reflective pattern) to provide sample and patient identification and to allow a tissue processor to automatically recognize the geometry of the tissue chamber being used and to adjust input volumes accordingly, thereby further minimizing wasted reagents. In various embodiments, the vessel itself may be color coded to indicate geometry. Similarly, microscope scanning and imaging time can also be reduced with sample-specific sized chambers. While microscope slide scanners use various approaches to minimize slide scanning time, they are still inefficient and manually dependent to varying extents. Current systems typically take a low power image and use image processing algorithms to estimate the position and size of the tissue, but they are adversely affected by difficult-to-control artifacts such as mounting variability, dirt, and smudges. As a result, manual supervision is required to ensure tissue is not missed and that large empty spaces are not imaged. Operator adjustment of scanning area is a time-consuming component of slide scanning which can result in repeat scans and high average slide scan times.

Coded, sample-size specific chambers as described herein can help avoid manual interventions while maximizing efficiency for image scanning. Because a tissue is placed in the smallest chamber in which it fits and the imager is able to read the chamber coding to determine the size of the region to scan, the entire possible tissue location region is imaged. The chance for error can be reduced and operator intervention should not be required, providing efficient imaging with reduced labor costs and errors.

Tissue chambers may include a trough area or cavity cutaway sized to contain a sample and various processing fluids wherein processing of the sample occurs. The trough may be in fluid communication with one or more fluid inlets or outlets operable to provide processing fluids to the trough. The tissue chamber may comprise additional material surrounding the trough to allow for ease of manipulation and/or orientation of the chamber within various processing apparatuses. Tissue chambers can include one or more locating members such as a post configured to fit within a corresponding recess in various processing apparatuses to thereby locate the tissue chamber relative to fluid inlets/outlets, imaging objectives, wax removal tools, or other items. In various embodiments, the locating member may be on the processing apparatus and the tissue chamber may comprise a corresponding recess to receive the member.

Tissue chambers may comprise a frangible area in the floor or walls of the trough to provide a controlled separation of the floor or wall from the remainder of the tissue chamber upon the application of sufficient force thereto. Such a frangible area may comprise a region of thinner or weaker material and can allow for efficient machine separation of an oriented, wax-embedded sample from the tissue chamber.

Tissue chambers can include wax-retention members within the trough such as barbs configured to stabilize the wax-embedded sample within the trough during processing.

Aspects of the invention include a container for holding a tissue sample with the container comprising a cavity or trough for receiving a tissue sample and a wall having an interior surface adjacent to the cavity and an exterior surface. In some embodiments, the chamber is loaded on the imaging side and an optically transparent imaging cover or sheet may be affixed after tissue loading in such a manner that the tissue is not easily moveable in any direction while rendering the chamber substantially sealed to liquid and air. In another embodiment the tissue can be loaded into a cavity on the surface opposite the imaging surface and adjacent to the underside of the imaging surface. A cover can be placed over the cavity after the tissue is loaded in order to render the tissue substantially immovable within the chamber and to substantially seal the chamber to liquid or air. The wall may include an optical window with the window comprising a plurality of features on the interior surface configured to contact the tissue sample and permit fluid flow between the tissue sample and the window. In some embodiments the surface opposite the optical window (e.g. is also optically transparent or transmissive of specific wavelengths and may be used as an imaging window. The transmissive wavelengths may be those corresponding to precisely half the wavelength (twice the frequency) of the excitation laser wavelength, as would be generated by second harmonics (second harmonic generation).

The optical window can include a refractive index approximately equal to a refractive index of a fluid in which the tissue sample is immersed prior to imaging (e.g., a clearing solution). The refractive index of the clearing solution or other fluid to be used in processing the tissue sample may be approximately equal to the refractive index of a structure of the tissue sample to be analyzed. The optical window can comprise a refractive index of about 1.5 to about 1.7.

The size of the chamber may be any size which accommodates a tissue sample for microscopic analysis. In various embodiments the external planar dimensions of the chamber are approximately those of a microscope slide, generally approximately 2.5 mm×75 mm or 1 inch by 3 inches. The imaging portion of the chamber may be substantially smaller in some embodiments. For example, the imaging portion of a chamber for prostate core biopsies may be between about 1 mm×15 mm and about 3 mm×40 mm, thereby fitting in a chamber with the external dimensions of a standard microscopy slide. In some embodiments the planar dimensions may be larger so as to accommodate specific specimen types having dimensions larger than the above-referenced core biopsies. For example, for imaging of an eye enucleation specimen, the chamber may have dimensions of between about 25 mm×25 mm and about 50 mm×50 mm. In other embodiments, the imaging chamber dimensions can be large enough to accommodate specimens typically referred to as large format histology specimens, or "whole mounts", which are in the range of about 65 mm×50 mm in planar dimension. Similarly, the imaging chamber height may be any height required for accommodating a specific specimen type. For example, heights may be anywhere between about 200 µm and about 15 mm. In some embodiments, the imaging chamber may be between about 200 µm and 500 µm in height, best suited for cytology specimens and very small biopsies. In other embodiments the chamber height may be between about 500 µm and 1.5 mm, typically best suited for small and core biopsies.

Incorporation of a sponge support as discussed above may require a taller chamber height to accommodate both the sponge and the specimen. For example a chamber incorporating a sponge support may have a height of between about 1 mm and about 3 mm for small and core biopsies. In other embodiments, the chamber height can be between about 3 mm and about 6 mm, which may be best suited for regular tissue sections. In still other embodiments, the chamber height can be between about 6 mm and 15 mm, dimensions which may accommodate large format histology specimens as well general intermediate to large un-sectioned samples.

The external dimensions of a container comprising the chamber can vary depending on the dimensions of the enclosed tissue chamber and will be large enough to allow for any required fluid channels or external port plugs as described herein. In some embodiments the external dimensions of the container may include a height between about 1 mm and 10 mm. In other embodiments the container height may be between about 500 µm and 1 mm. In other embodiments the container height can be between about 10 mm and 20 mm.

The plurality of features may comprise a material having a refractive index approximately equal to a refractive index of a fluid in which the tissue sample is immersed prior to imaging (e.g., a clearing solution). In certain embodiments, the refractive index of the clearing solution or other fluid to be used in processing the tissue sample may be approximately equal to the refractive index of a structure of the tissue sample to be analyzed.

The plurality of features can comprise a material having a refractive index of about 1.5 to about 1.7. The plurality of features may comprise a material having a refractive index of between about 1.53 and about 1.60. The plurality of features can comprise a material that dissolves in the presence of an organic solvent. The organic solvent may be a clearing solution such as benzyl alcohol and benzyl benzoate (BABB).

In various embodiments, the container may comprise a porous compressible material configured to contact the tissue sample on a side opposite the optically clear window. In some embodiments the porous compressible material is a plastic sponge. The sponge cell size may be any size that enables adequate tissue support with minimal compression and may be anywhere in the range of 10 µm to 5 mm. The sponge cell size may be in a range that helps wet both the tissue and optical surfaces without air bubble trapping. In preferred embodiments, the sponge cell size is between 50 and 500 µm when dry. In other preferred embodiments the sponge cell size is between 50 and 200 µm. The sponge may be open cell or closed cell. In preferred embodiments the sponge is open cell. In preferred embodiments the sponge is substantially non-fluorescent. In some embodiments the sponge is fabricated from a material that has a refractive index between about 1.45 and about 1.7. In some embodiments the sponge has a refractive index of between about 1.53 and 1.60. The sponge material may be selected to approximately match the refractive index of the cleared tissue sample to be imaged.

The container may comprise one or more fluid ports in fluid communication with the cavity for receiving the tissue sample and a space outside the chamber. In preferred embodiments the chamber contains two ports. The two ports may be on the same surface, facilitating connection to a fluid exchange system or processor. In preferred embodiments the fluid ports are self-sealing, such as with a rubberized or silicone plug or surface that permits introduction of a needle but which seals upon needle removal. In some embodiments the self-sealing ports are needle-free connectors, such as those that include a self-closing valve that opens when a tube connector is attached.

The container can comprise a material that is resistant to acid, a material that is resistant to organic solvents such as BABB, a material that is resistant to alcohols and/or a material that is resistant to temperatures up to about 75 degrees Celsius. The sponge can comprise a material that is resistant to acid, a material that is resistant to organic solvents such as BABB, a material that is resistant to alcohols and/or a material that is resistant to temperatures up to about 75 degrees Celsius.

In some embodiments, the cavity for receiving tissue samples may comprise a frangible area. The frangible area can be located at a perimeter of the wall of the cavity. The frangible area may comprise an area of thinned material relative to a remainder of the wall of the cavity.

The container may comprise one or more wax-retention members extending from the interior surface of the wall and/or one or more locating members extending from the exterior surface of the wall.

Aspects of the invention may include a method for analyzing a tissue sample including steps of orienting a tissue sample in a tissue chamber in a desired position; exposing the tissue sample to a first solution for chemical processing in the desired position in the tissue chamber; exposing the tissue to a fluid in which the tissue sample is immersed prior to imaging (e.g., a clearing solution) in the desired position in the tissue chamber; imaging the tissue sample in the desired position in the tissue chamber; and/or wax embedding the tissue sample in the desired position in the tissue chamber.

The clearing agent may be BABB. The first solution may comprise a dehydrant, a fixative, a dye, and/or some combination thereof including where the fixative may be a dehydrant. In certain embodiments, the dye may be a fluorescent dye and the imaging step can comprise fluorescent imaging. The desired position may be a desired position for sectioning of the wax-embedded tissue sample and or imaging of the tissue sample. The tissue chamber can comprise a plurality of features disposed on an interior surface of the tissue chamber and configured to contact the tissue sample and permit fluid flow between the tissue sample and the interior surface.

DETAILED DESCRIPTION

The present invention provides apparatuses, systems, and methods for the visual histologic analysis of tissue during chemical processing (e.g., fixing, dehydrating, dying, and staining) and wax embedding while reducing manual intervention, human contact, and labor costs during processing. Systems and methods allow for initial placement of a tissue sample in a single container in a preferred orientation for wax embedding and sectioning and/or imaging. The tissue sample can then be chemically processed (fixed, dehydrated, and/or dyed) and wax embedded in the single container without subsequent repositioning. Furthermore, the tissue sample can be dyed, cleared and imaged intact to provide an initial pathological analysis potentially negating the need for continued expensive processing, embedding, sectioning, staining, and analysis. Systems and methods of the invention allow for simple machine separation of the wax encased sample ready for sectioning in a microtome.

Figure 1:
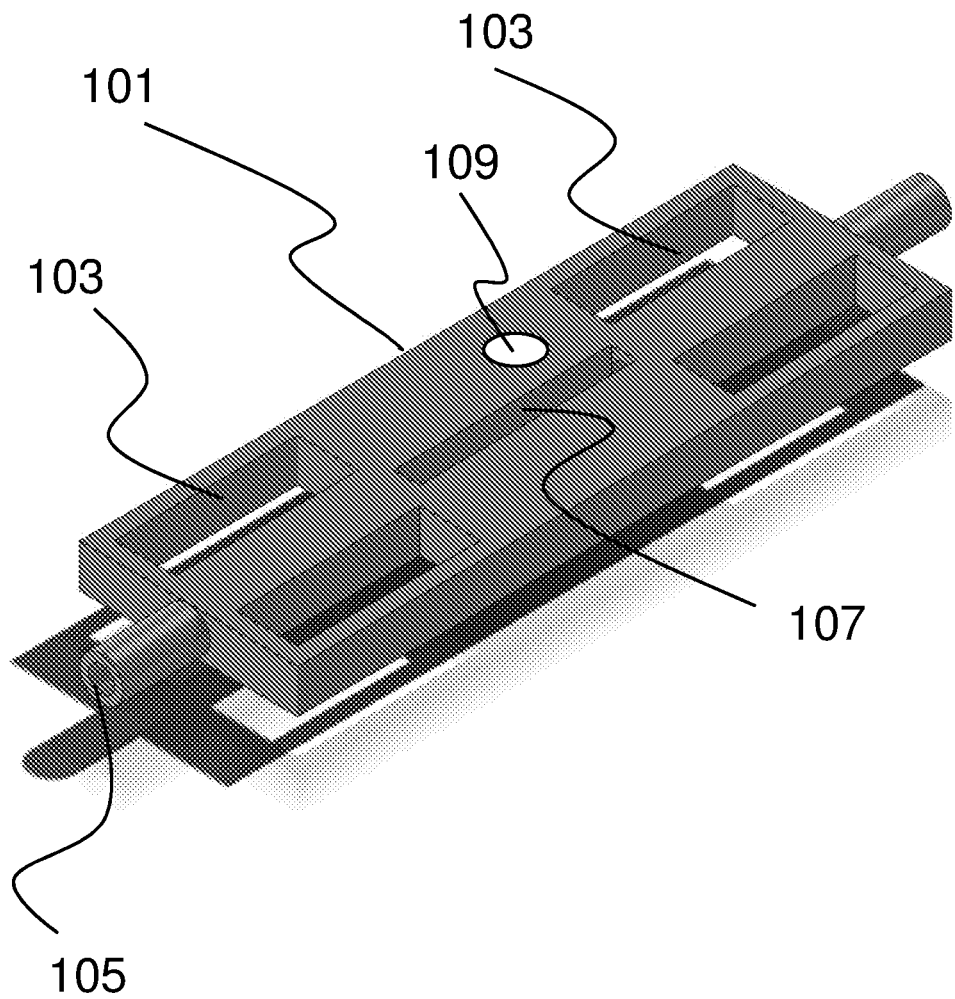
FIG. 1 shows a tissue chamber having a trough and fluid inlets and outlets.

FIG. 1 shows a tissue chamber 101 having a trough 107 for receiving and processing a tissue sample. Samples may be obtained, for example, during surgery, biopsy, fine needle aspiration, culture, or autopsy and are preferably obtained for histological analysis. Tissue chambers 101 and/or troughs 107 therein may be provided in a variety of sizes and may include a mark 109 (human and/or machine-readable) that can correspond to the trough 107 or chamber 101 size and/or provide information regarding the subject from which the sample was obtained, the type of sample, and/or the type of analysis to be performed. Once read by a machine or human, the mark 109 may be used to tailor tissue processing (e.g., reagent selection, reagent volumes, or processing apparatus selection and configuration) and/or to label imaging data.

Tissue chambers 101 may include a remainder area surrounding the trough 107 to increase the overall size and allow for ease of manipulation. Cutaways 103 or openings in the chamber 101 can reduce the mass of the chamber 101 along with reducing the required material in production, time of production, and the associated costs thereof. One or more fluid inlets/outlets 105 are in fluid communication with the trough 107 and an outside surface of the chamber 101. The fluid inlets/outlets 107 can interface with the corresponding fluid inlets/outlets in various processing apparatuses to provide and remove processing fluids such as fixatives, dehydrating fluids, stains/dyes, clearing solution, or wax for embedding.

The walls of the tissue chamber or relevant portions thereof (e.g., an imaging window) may be optically clear and/or index matched to the clearing solution and/or the sample structures to be measured. The tissue chamber 101 is thereby operable to contain a tissue sample for all processing steps for histological analysis while allowing for periodic imaging of, for example, an intact and wax-free sample including fluorescent dye-based imaging techniques. After dying, fixing, dehydrating, and/or any other processing steps are performed, wax can be introduced to the trough 107 via the fluid inlets/outlets 105 to provide a wax-embedded sample in a block of wax ready for sectioning and subsequent analysis.

Accordingly, a tissue sample can be initially oriented within the trough 107 in the desired position for both initial imaging and later sectioning and then left untouched throughout the remainder of the processing, imaging, wax embedding and removal steps.

Tissue chambers may be constructed of materials such as metals, plastics, a cyclic olefin polymer, or glass. Preferably the chamber material does not react with the tissue sample or any of the processing solutions with which its surfaces come in contact. Chambers can be constructed of multiple materials in certain embodiments. For example, the trough may be constructed of an unreactive and index matched material but, to reduce costs, the remainder of the chamber may be constructed of a different, cheaper material.

Figure 2:
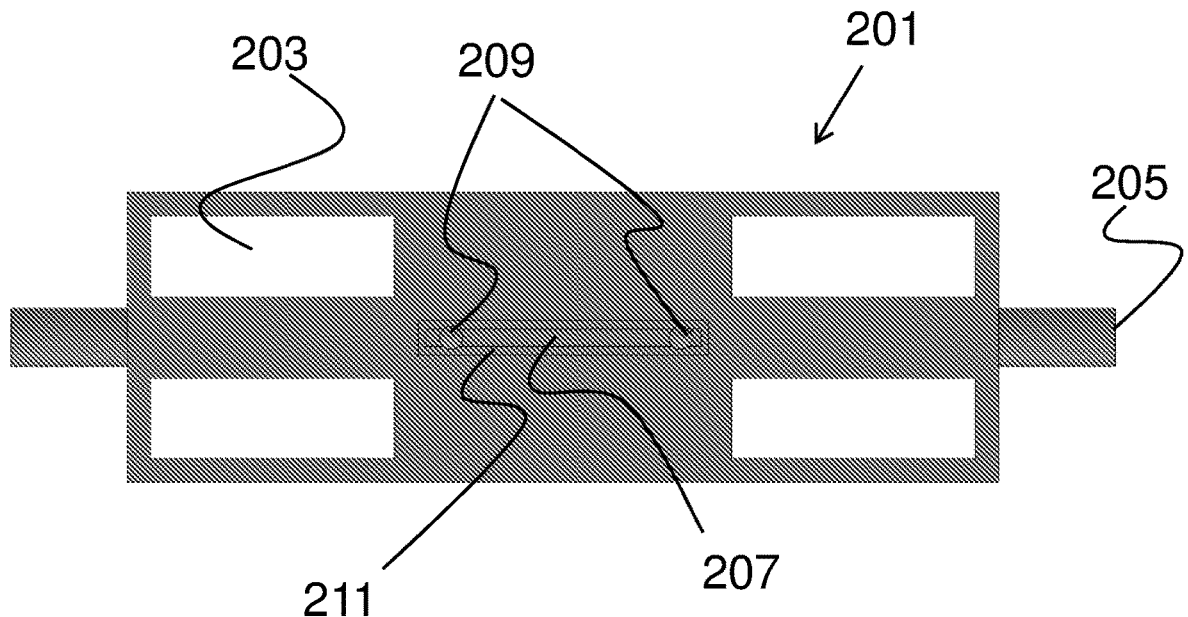
FIG. 2 shows a top view of a tissue chamber having wax-retention members.

FIG. 2 shows a top view of a tissue chamber 201 with fluid inlets/outlets 205, cutaways 203 and a trough 207. Within the trough 207 may be wax-retention members 209 such as barbed posts configured to locate and retain hardened wax and a sample held therein to a floor of the trough 207. The trough 207 can include a frangible area 211 on its floor consisting of, for example, an area of thinner or weaker material such that, upon application of a shear force between the floor of the trough 207 and the remainder of the chamber 201, the floor of the trough 207 will separate from the remainder of the chamber 201 along the lines defined by the frangible area 211. The frangible area 211 can be sized and located to comprise the floor of the trough 207 and the wax-retention members 209 such that, upon separation along the frangible area 211, a wax-encased sample, coupled to the floor of the trough 211 can be removed from the remainder of the chamber 201 for further processing (e.g., sectioning in a microtome). The wax-retention members 209 can be spaced in a manner such that relevant samples can be fit between them in the trough 207 if necessary.

Figure 3:
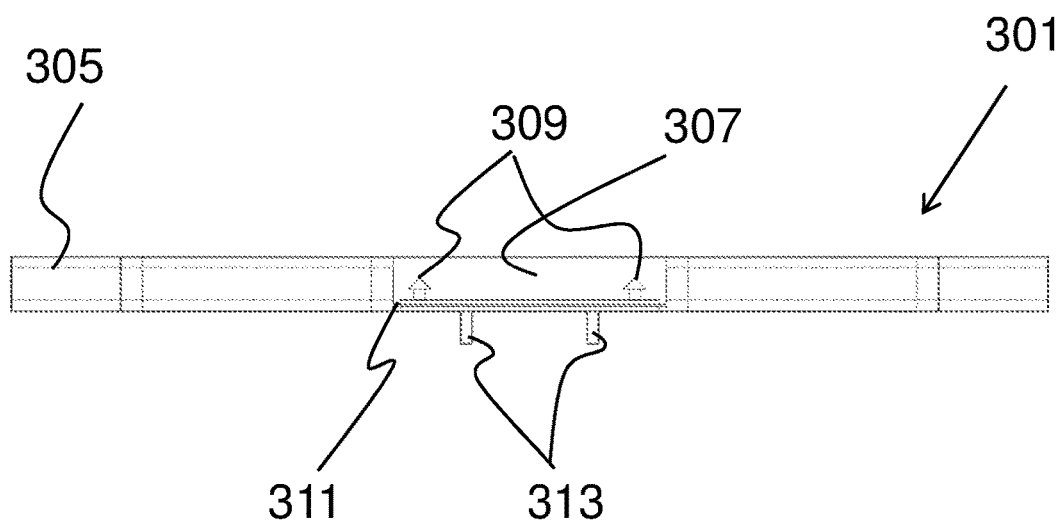
FIG. 3 shows a cutaway view of a tissue chamber with locating members and wax-retention members.

FIG. 3 shows a cutaway view of a tissue chamber 301 with fluid inlets/outlets 305 shown providing fluid access to the trough 307 from the outside surface of the chamber 301. The trough 307 comprises wax-retention members 309 as well as a frangible area 311 as described above. The bottom surface of the trough 307 can comprise locating members 313 such as posts or tabs (or corresponding recesses for receiving such members). The locating members 313 may correspond to complimentary locating recesses on the surface of various processing and imaging apparatuses. It will be readily apparent that while described herein with respect to the members being present on the chamber 301 and the corresponding recesses being present on the apparatuses, the reverse arrangement would also provide the same function. The locating members 313, when positioned in their corresponding recesses, may serve to locate the chamber 301 and the trough 307 within the apparatuses relative to, for example, a fluid coupling for the fluid inlets/outlets 305, a wax-cutting blade, a plunger for separating the trough 307 floor along the frangible area 311, an imaging objective, a light source, or various other processing tools.

In certain embodiments, the locating members 313 are attached to the floor of the trough 307 and remain so after separation at the frangible area 311 resulting in a wax-embedded sample, in a wax block secured to the now separated trough 307 floor by wax-retention members 309 and locatable by locating members 313 protruding from the surface of the trough floor 307 opposite the surface retaining the wax-embedded sample. The locating members 313 can therefore be used to locate the wax block containing the sample for subsequent processing for example in a microtome for sectioning. Tissue chambers may be reusable or single-use items. For example, frangible tissue chambers are generally considered single-use items.

Figure 4:
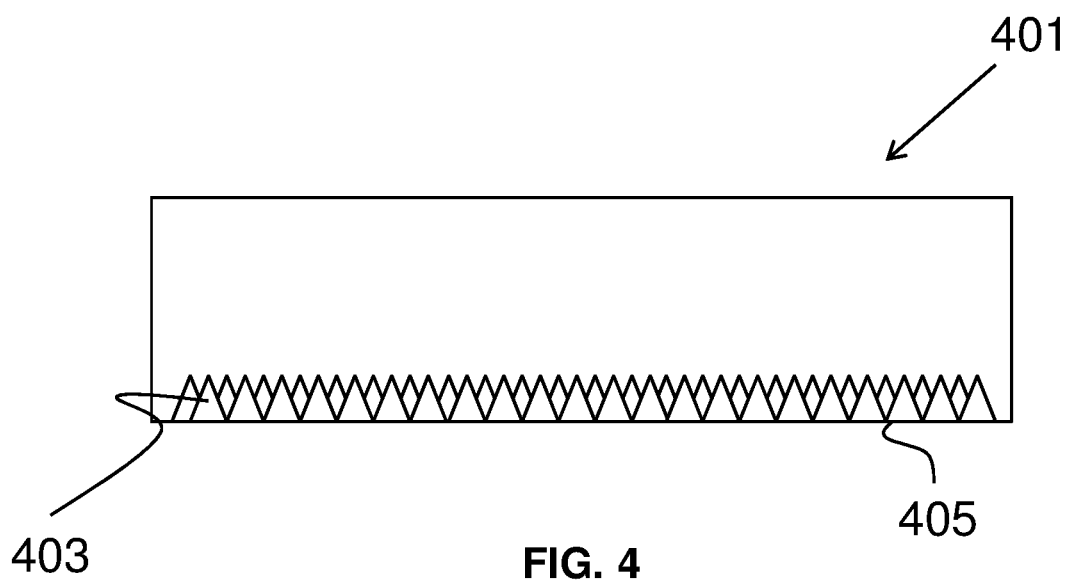
FIG. 4 shows a tissue chamber having a plurality of features for spacing a sample away from the chamber wall.

FIG. 4 shows a tissue chamber 401 having a plurality of features 403 for spacing a sample away from the chamber wall 405. Spacing the sample away from the otherwise flat surface of the chamber wall 405 allows for processing solutions such as dehydrating, fixing, clearing, and dye solutions, to access all sides of the sample. In the absence of such features 403 the sample would rest against the flat surface of the chamber wall 405 sealing it off from the fluids and increasing processing times, reducing processing effectiveness (and subsequent analysis quality), and/or requiring manipulation or agitation to re-orient the sample and expose the obstructed surfaces to the fluids. Features may be of any shape including cones, pyramids, needles, cylinders, spheres, cubes, ridges, spikes, or other 3-dimensional shapes. Features may include porous structures or recesses in a material surface to allow fluid penetration or access. As the features 403 are designed to reduce surface area contact between the sample and the vessel or chamber wall 405, shapes such as cones or pyramids that provide a large base area in contact with the chamber wall 405 with a minimal contact point at the top supporting the sample are preferable. Features 403 should be shaped and spaced such that they provide the minimal contact surface area with the sample while still supporting the sample above the surface of the wall 405 and enough weight distribution so as not to puncture or otherwise penetrate the sample.

The features should have a height or depth sufficient to allow fluid to flow between the supported sample and the surface of the chamber wall. In various embodiments, features may have a height or depth about 1 μm to about 5 mm.

An apparent drawback to such features 403 would be their deleterious effects on imaging quality. Accordingly, in various embodiments the features may be constructed of a material similar to the wall 405 of the chamber 401 and be index matched to the clearing solution and/or the sample structures to be examined. The features 403 will thereby provide minimal distortion during imaging. In other embodiments, the features 403 may be constructed of a material different from the walls 405 of the chamber 401 and that material may be configured to dissolve in the presence of one or more of the processing solutions (e.g., the clearing solutions). Because the clearing solution is generally applied before imaging, if the features 403 dissolve in the presence of the clearing solution, they will not be present to distort the subsequent imaging. Clearing solutions may comprise benzyl alcohol and benzyl benzoate (BABB) and, accordingly, features 403 may comprise materials known to dissolve in BABB.

Processing devices of the invention may include wax removal devices operable to manipulate tissue chambers described herein. Such devices can comprise a base with a spring-loaded platform on which the tissue chamber may be placed. There may be a hole in the middle of the platform to accommodate a plateau shaped to match the base of the sample trough that includes positioning holes that match the positioning posts on the bottom of the tissue chamber. When pressed from above, the tissue chamber can be lowered on the spring loaded platform such that the central plateau presses up against the bottom of the sample trough, breaking it along the thinned perimeter and thus releasing the sample from the chamber.

The wax removal device can also include a central piston that holds two knives pointing down towards the ends of the sample trough from above. When lowered, these knives cut into the wax, separating the portion of wax within the sample trough from the wax that extends into the fluid inlet and outlet.

The wax removal device may be operable through three positions (actuated machine or manually via a handle). An open position, in which the arm is raised, may lift both the central piston and the larger chamber piston above the base enough to enable placement of the tissue chamber onto the base. A wax cutting position can be where the pistons have been lowered in unison by the arm to the point where the knives in the central piston have cut through the wax. Stops on the guide rails of the base can prevent the central piston from descending any further into the tissue chamber base. A wax removal position, where the arm is lowered further such that the larger chamber piston has pushed the tissue chamber down can force the sample trough base to break free of the tissue chamber. A spring mechanism on the insert that connects the handle to the central piston can enable the movement to the wax removal position while the central piston remains still, pressed against the stops.

After moving to the wax removal position and breaking the sample trough, the arm may be raised back to the open position and the sample/wax/trough base removed. The sample would then be ready for placement into a microtome for cutting.

Figure 5:
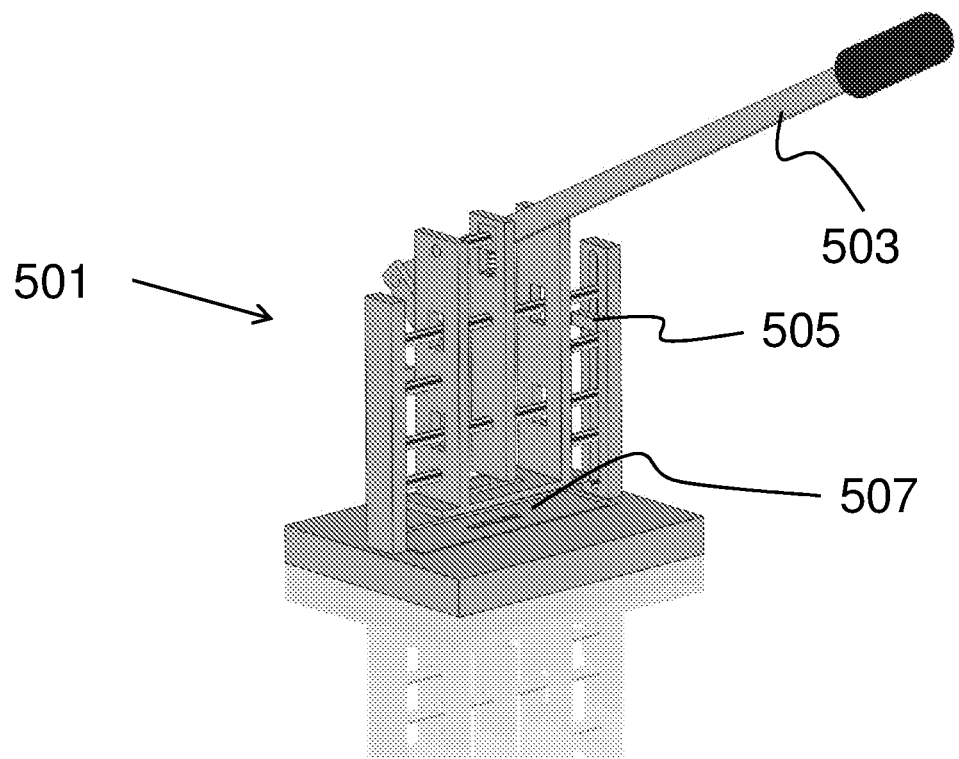
FIG. 5 shows a wax removal device in the open position.

FIGS. 5-8 show a wax removal device according to certain embodiments of the invention and configured to work with tissue chambers described herein. Wax removal devices are useful for removing a wax embedded sample from a tissue chamber after wax embedding. FIG. 5 illustrates a wax removal device 501 in an open position with the handle 503 in a raised position providing access to the spring-loaded platform 507 for the placement of a tissue chamber 509 thereupon. The spring-loaded platform 507 consists of an outer portion, the size and shape of which generally conforms to the dimensions of the tissue chamber 509 placed thereupon and is configured to support said tissue chamber 509 from below. The spring-loaded platform 507 also comprises an inner portion, the size and shape of which generally conform to the dimensions of a frangible trough portion of the tissue chamber 509 containing the wax-embedded sample 511.

The inner portion is solidly supported from below while the outer portion may be supported from below by springs or be otherwise capable of being depressed below the level of the central portion in response to a downward force on the spring-loaded platform 507.

The handle 503 is operably associated with a central portion 513 having wax-cutting blades 517 at the end proximal to the spring-loaded platform 507. The handle 503 is operable to apply downward force on the central portion 513 and, accordingly, the wax-cutting blades 517 toward the spring-loaded platform 507 and a tissue chamber 509 placed thereupon. The tissue chamber 509, the spring-loaded platform 507, and the wax-cutting blades 517 are located relative to each other such that when the handle 503 is operated, the wax-cutting blades 517 are forced into and through the wax in the tissue chamber 509 to cut the wax-embedded sample 511 out from surrounding wax in the tissue chamber 509. The wax removal device 501 comprises stops 505 operable to limit the downward motion of the central portion 513 and the associated depth reached by the wax-cutting blades 517 so that the wax-cutting blades 517 cut only through wax inside the tissue chamber 509 but do not cut through the floor of the tissue chamber 509.

The handle 503 is also operably associated with an outside portion 515 having a plunger 523 at the end proximal to the spring-loaded platform 507. While the stops 505 limit the downward motion of the central portion 513, the outside portion 515 is able to continue its downward motion in response to further operation of the handle 503. The plunger 523 generally conforms to dimensions of the outer portion of the spring loaded-platform 507 and comprises an opening that generally conforms in size and shape to the dimensions of the central portion of the spring-loaded platform 507. Accordingly, when forced down into contact with a tissue chamber 509 on the spring-loaded platform 507, the plunger 523 applies downward pressure only to the outer portion of the spring-loaded platform which in turn is depressed below the level of the rigidly supported inner portion. The inner portion thereby applies an upward force to the frangible trough portion of the tissue chamber 509 containing the wax-embedded sample 511 while the plunger applies a downward force to the remainder 525 of the tissue chamber 509 surrounding the trough portion. These opposing forces create a shear force at the thinned or otherwise frangible area such that the frangible area breaks, freeing the cut wax-embedded sample 511 from the tissue chamber 509.

Accordingly, full motion of the handle 503 is operable to move both the central portion 513 and outside portion 515 downward toward the spring-loaded platform 507. The wax-cutting blades 517 cut the wax surrounding the wax-embedded sample 511 and are stopped while the outside portion 515 and associated plunger 523 continue downward, breaking the remainder 525 of the tissue chamber away from the cut wax-embedded sample 511 and pushing the remainder 525 and the outer portion of the spring-loaded platform 507 down below of the level of the now separated was-embedded sample 523 which can then be removed from the wax removal device 501 for further processing.

Figure 6:
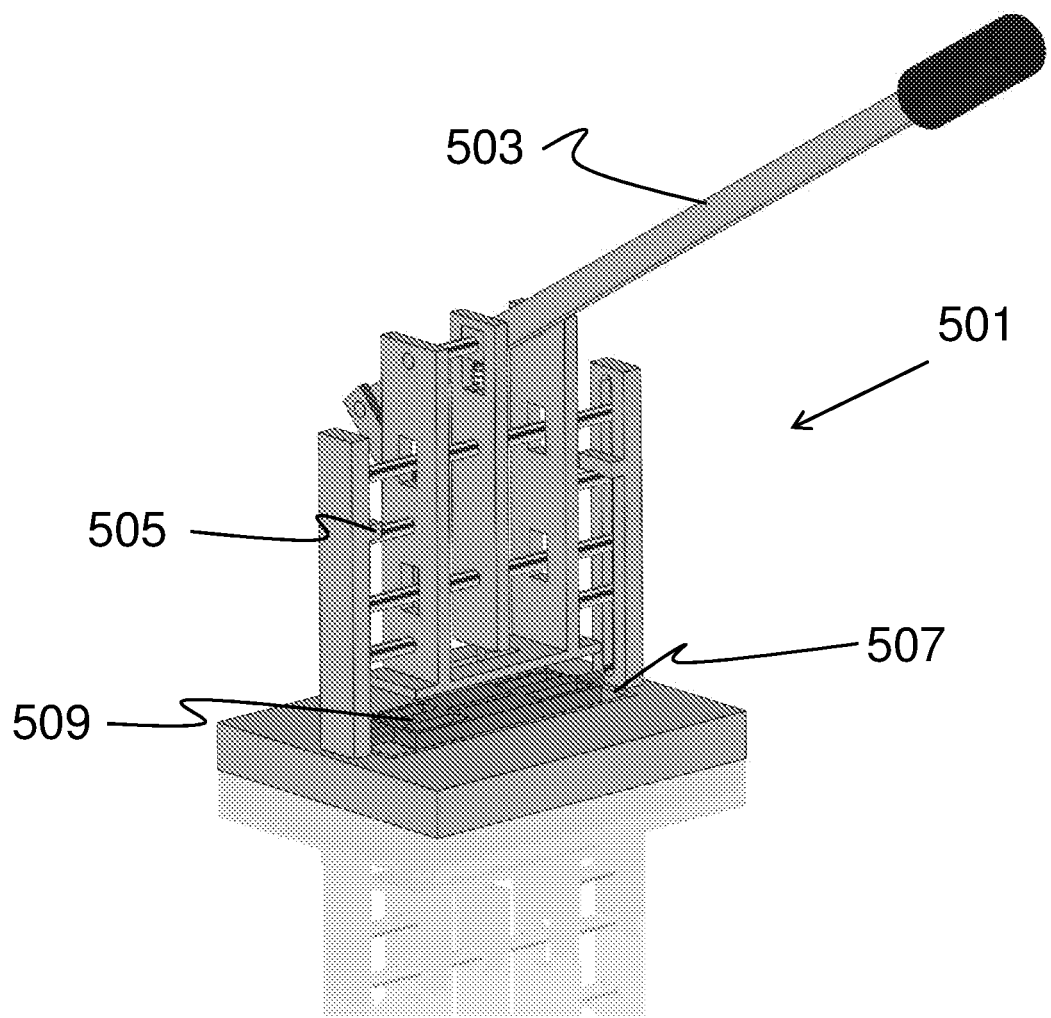
FIG. 6 shows a wax removal device in the open position with a tissue chamber loaded therein.

FIG. 6 shows the wax removal device 501 in the open position with a tissue chamber 509 positioned on the spring-loaded platform 507. The handle 503 is still in the raised position.

Figure 7:
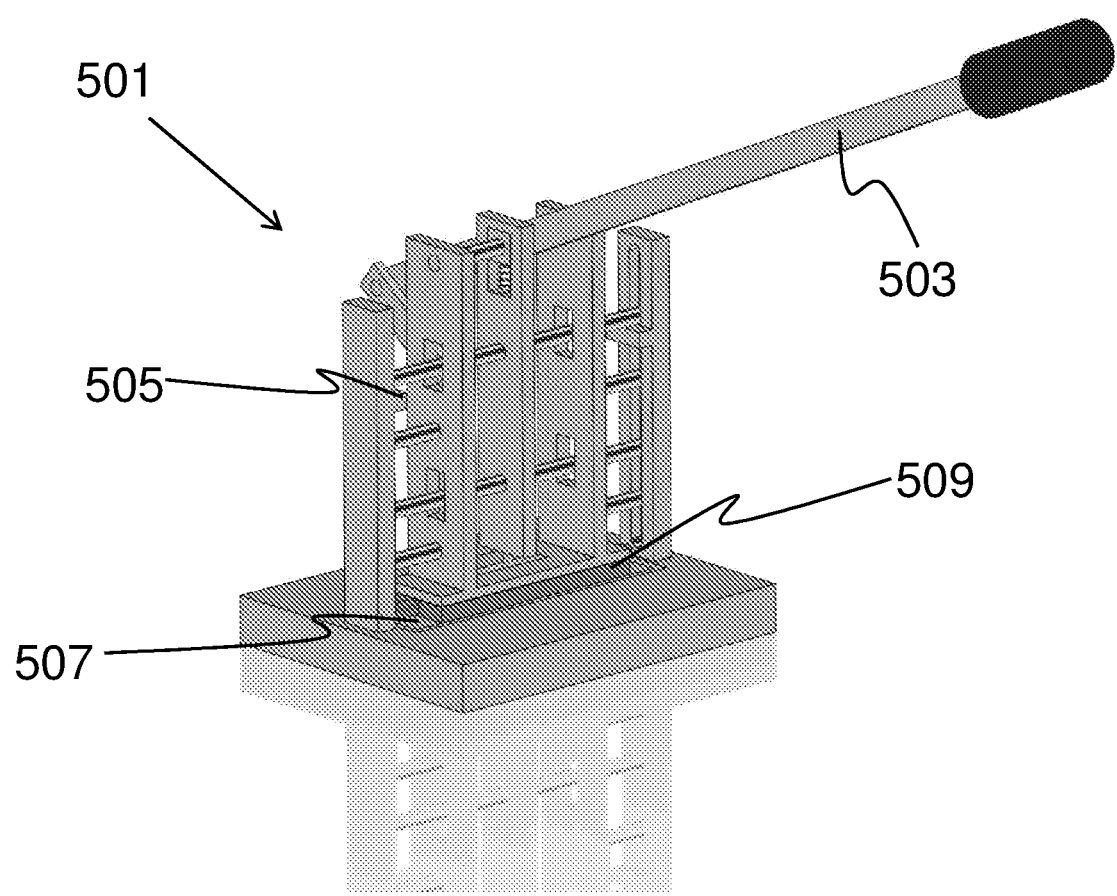
FIG. 7 shows a wax removal device in the wax cutting position.

FIG. 7 shows the wax removal device 501 in the wax cutting position where the handle 503 has been partially operated such that the stops 505 are acting on the central portion 513 and the wax-cutting blades 517 have cut the wax surrounding the wax-embedded sample 511 but the plunger 523 has not broken the frangible area of the tissue chamber 509.

Figure 8:
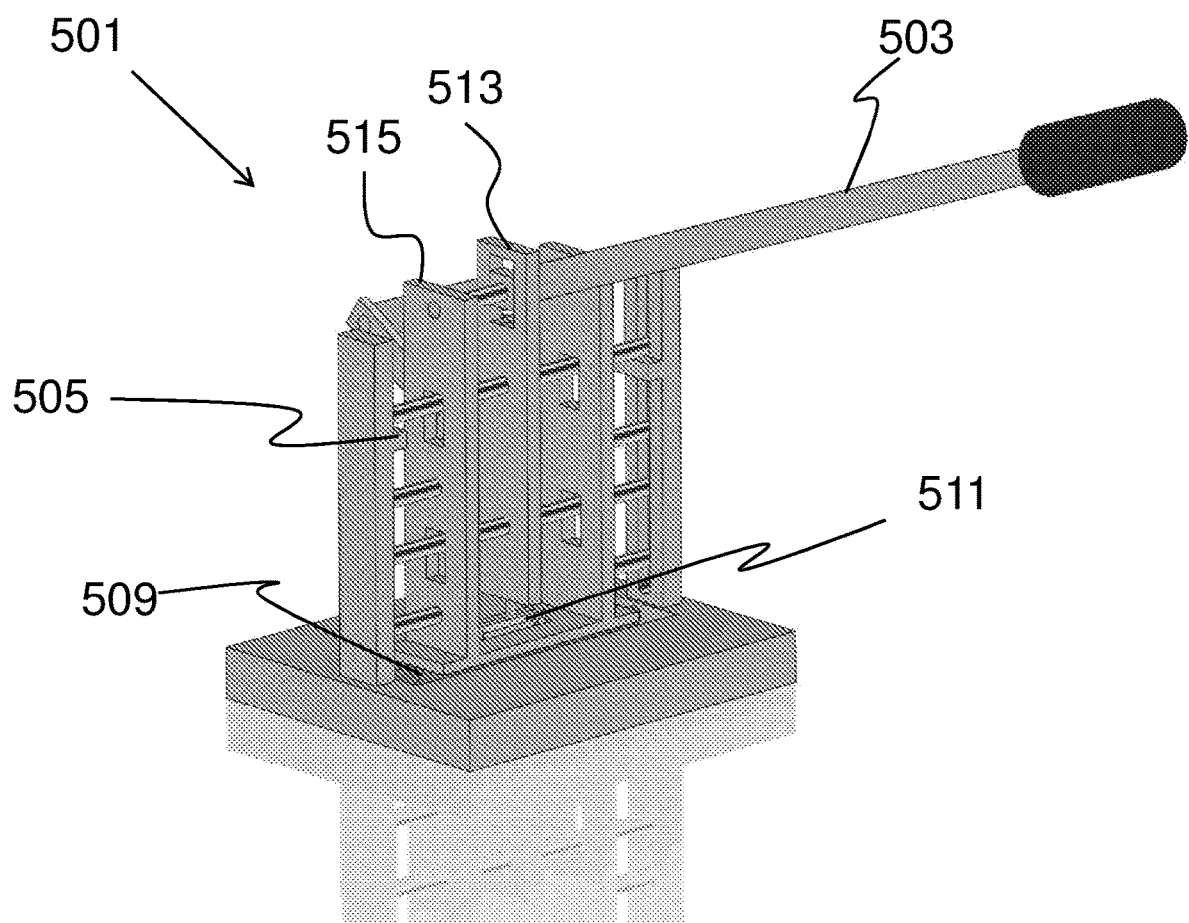
FIG. 8 shows a wax removal device in the wax removal position.

FIG. 8 shows the wax removal device 501 in the wax removal position where the handle 503 has been fully operated such that the outside portion 515 has forced the plunger 523 downward, breaking the remainder 525 of the tissue chamber downward on the spring-loaded platform 507 and apart from the now separate wax-embedded sample 511.

Figure 9A:
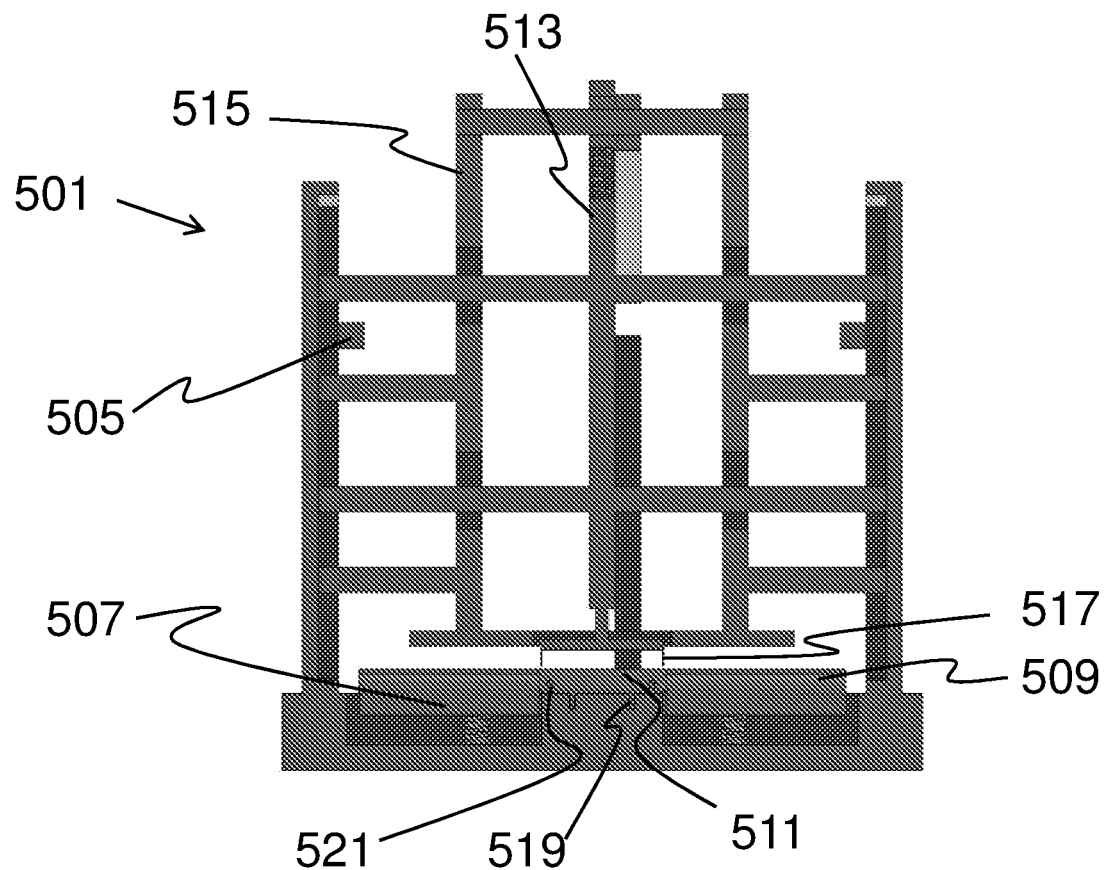
FIG. 9A shows a cutaway view of a wax removal device in the open position with a tissue chamber loaded therein.
Figure 9B:
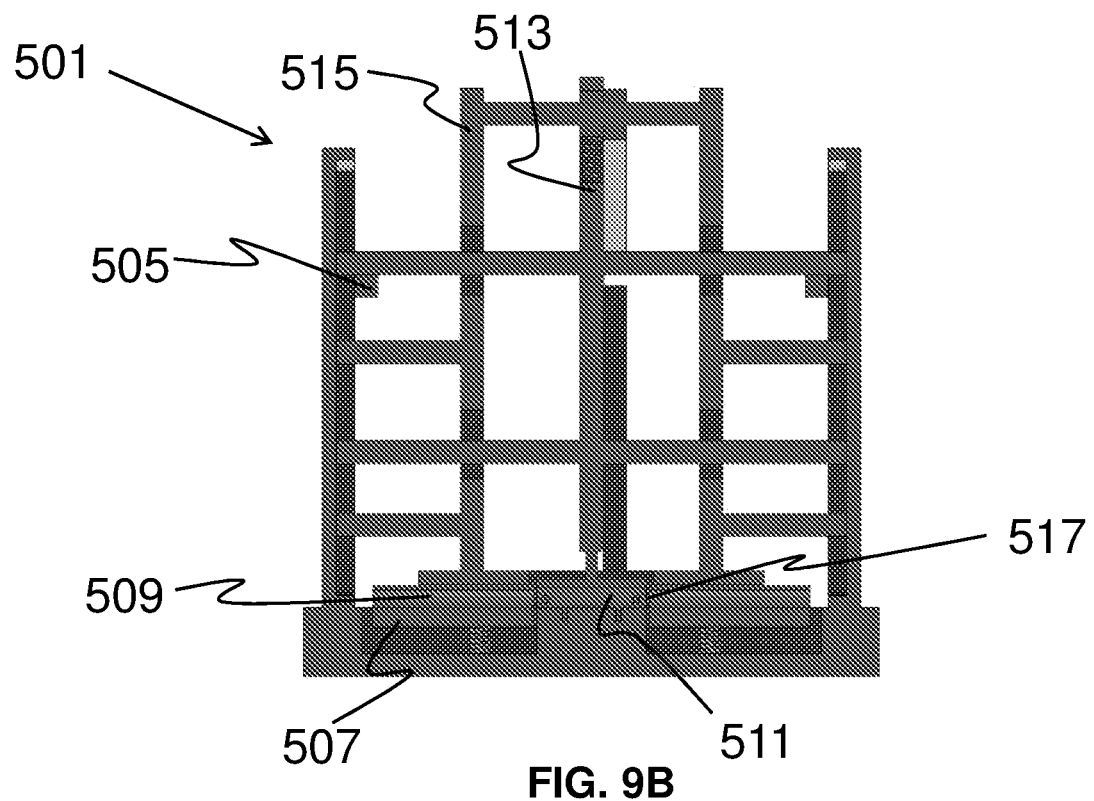
FIG. 9B shows a cutaway view of a wax removal device in the wax cutting position.
Figure 9C:
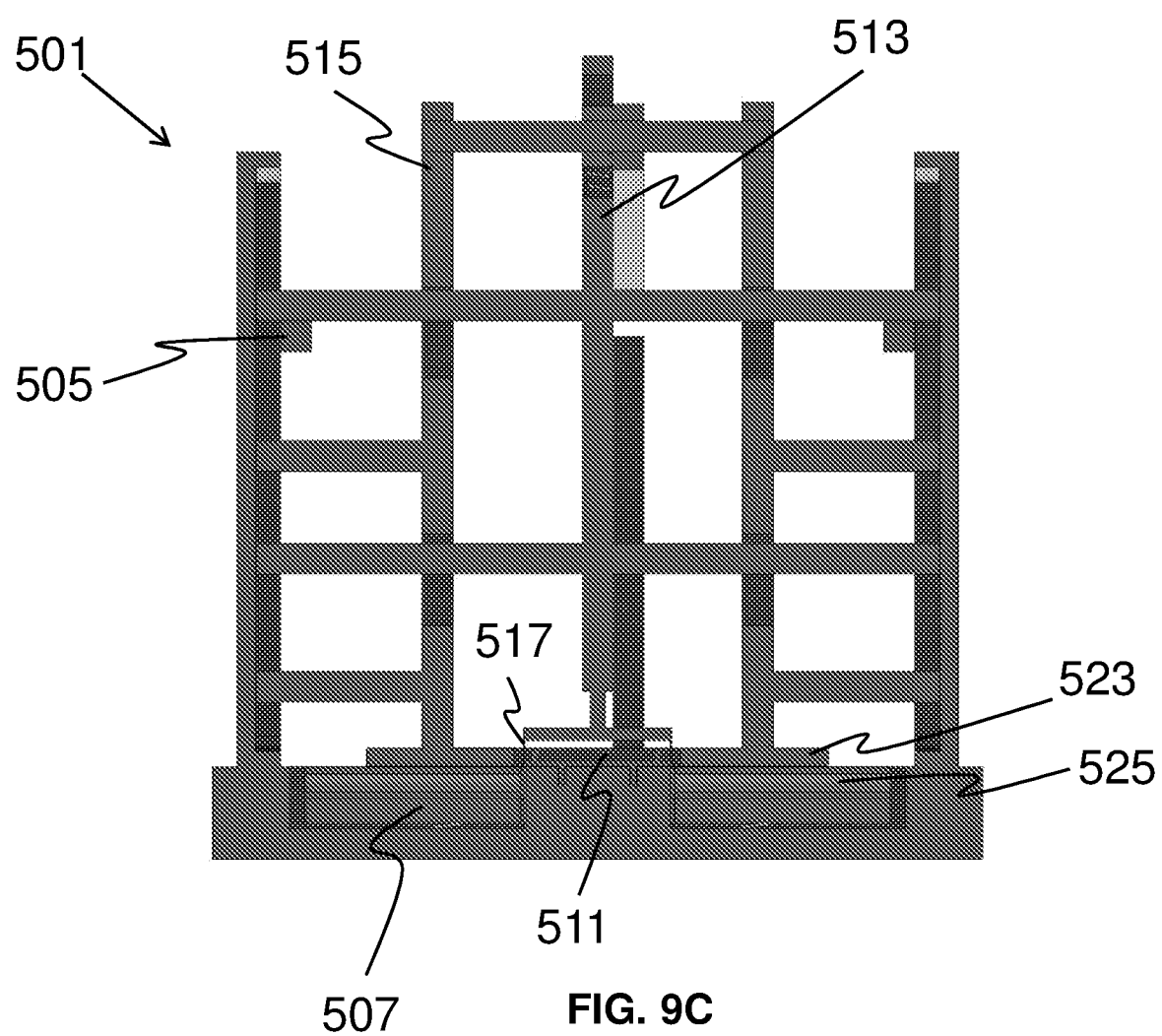
FIG. 9C shows a cutaway view of a wax removal device in the wax removal position.

FIGS. 9A-9C show a cutaway illustration of a wax removal device according to certain embodiments of the invention. The central portion 513 and outside portion 515 of the wax removal device 501 and their respective association with the wax-cutting blades 517 and the plunger 523 are shown. The cut away illustrations further show the inner and outer portions of the spring loaded platform 507 and the function of the wax removal device 501 to cut out the wax-embedded sample 511 and separate it from the remainder 525 of the tissue chamber for further processing.

As shown in FIGS. 9A-9C, the tissue chamber 509 and or the spring-loaded platform 507 may comprise locating posts, tabs, or other members 519 and complimentary recesses for accepting said locating tabs, posts, or other members. The locating members 519 and corresponding recesses can serve to locate the tissue chamber 509 on the spring-loaded platform 507 relative to the inner and outer portions thereof and also relative to the wax-cutting blades 517 and the plunger 523. Wax-retention members 521 (e.g., posts or barbs) are also shown in FIGS. 9A-9C as part of the tissue chamber 509. The wax-retention members 521 are operable to hold and locate the wax-embedded sample 511 within the tissue chamber 509 during operation of the wax removal device 501.

FIG. 9A shows the wax removal device 501 in the open position with a tissue chamber 509 loaded on the spring-loaded platform 507. FIG. 9B shows the wax removal device 501 in the wax cutting position where the stops 505 are acting on the central portion 513 and the wax-cutting blades 517 have cut the wax surrounding the wax-embedded sample 511 but the plunger 523 has not broken the frangible area of the tissue chamber 509. FIG. 9C shows the wax removal device 501 in the wax removal position where the outside portion 515 has forced the plunger 523 downward, breaking the remainder 525 of the tissue chamber downward on the spring-loaded platform 507 and apart from the now separate wax-embedded sample 511.

Figure 10:
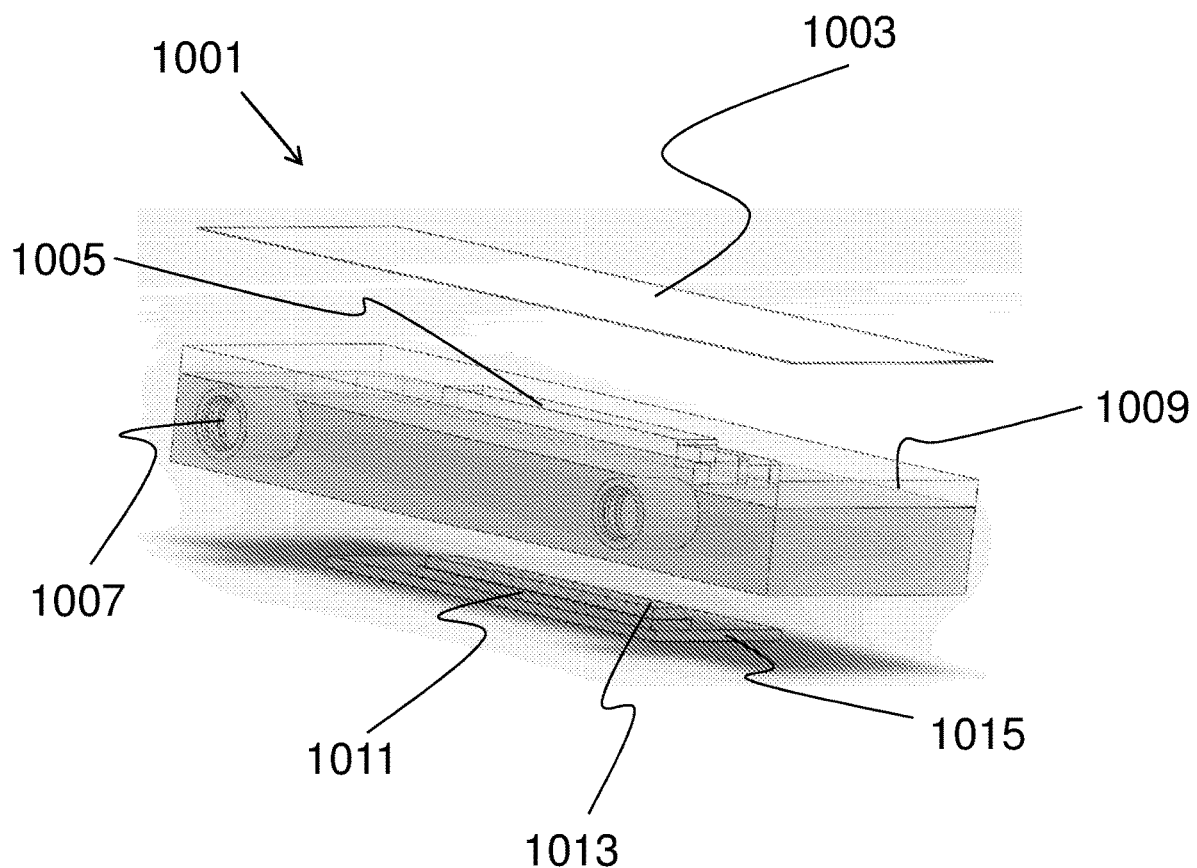
FIG. 10 illustrates a container 1001 including a support sponge 1013 according to certain embodiments.

FIG. 10 illustrates a container 1001 including a support sponge 1013 according to certain embodiments. The container 1001 includes a specimen chamber 1005 to receive a tissue sample as well as two fluid ports 1007 to introduce and remove fluid from the specimen chamber 1005.

The container 1001 includes a cover 1003 than encloses the specimen chamber 1005 after a tissue sample has been placed therein. The fluid ports 1007 may be self-sealing, especially where the cover 1003 is operable form a fluid and air tight seal with the top of the container 1001 to create a sealed environment within the specimen chamber 1005. As noted above, self-sealing fluid ports 1007 may include a rubberized or silicone plug or surface that permits introduction of a needle but which seals upon needle removal. In some embodiments the self-sealing ports are needle-free connectors, such as those that include a self-closing valve that opens when a tube connector is attached. The container 1001 may include a bottom cover 1015 with a sponge support 1013 or other support as discussed herein. The sponge support 1013 and/or the bottom cover 1015 may form the bottom of the specimen chamber 1005 and may comprise an optically transmissive, transparent, or index-matched material (e.g., having approximately the same refractive index as the cleared tissue sample to be imaged) such as a optically transmissive window 1011 in the bottom cover 1015.

A sponge or other porous compressible material is configured to contact the tissue sample and hold the tissue sample in place after positioning within a tissue chamber for chemical processing, clearing, and/or imaging. In some embodiments the porous compressible material is a plastic sponge. The sponge cell size may be any size that enables adequate tissue support with minimal compression and may be anywhere in the range of 10 µm to 5 mm. The sponge cell size may be in a range that helps wet both the tissue and optical surfaces without air bubble trapping. In preferred embodiments, the sponge cell size is between 50 and 500 µm when dry. In other preferred embodiments the sponge cell size is between 50 and 200 The sponge may be open cell or closed cell. In preferred embodiments the sponge is open cell. In preferred embodiments the sponge is substantially non-fluorescent. In some embodiments the sponge is fabricated from a material that has a refractive index between about 1.45 and about 1.7. In some embodiments the sponge has a refractive index of between about 1.53 and 1.60. The sponge material may be selected to approximately match the refractive index of the cleared tissue sample to be imaged. The sponge can comprise a material that is resistant to acid, a material that is resistant to organic solvents such as BABB, a material that is resistant to alcohols and/or a material that is resistant to temperatures up to about 75 degrees Celsius.

Figure 11:
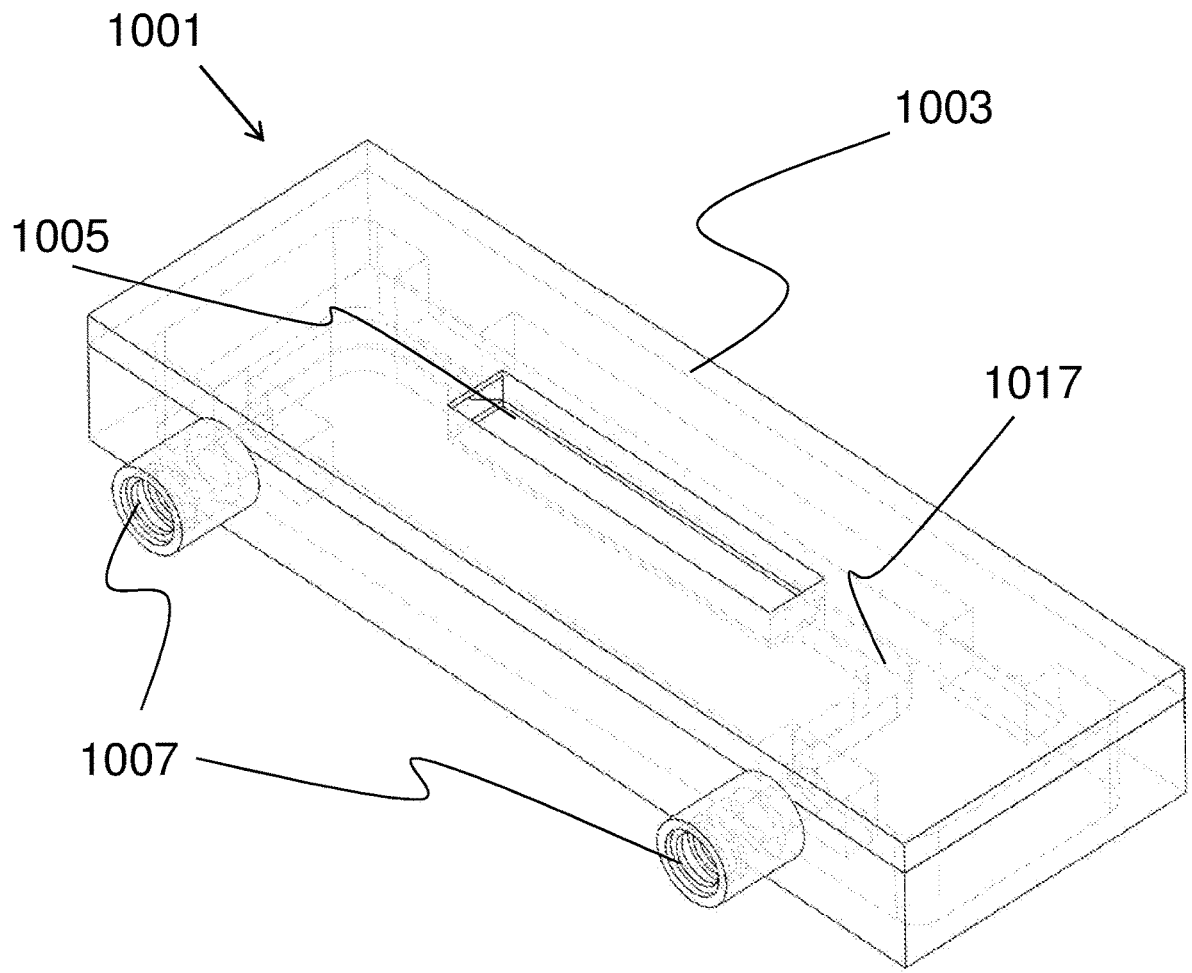
FIG. 11 illustrates some of the internal configuration of the container 1001 shown in FIG. 10.

FIG. 11 illustrates some of the internal configuration of the container 1001 shown in FIG. 10 including the internal fluid passages 1017 leading from the fluid ports 1007 to the specimen chamber 1005. The fluid ports 1007 is optionally positioned at a planar level offset from the level of the specimen chamber 1005, such that they can be oriented higher than the specimen chamber 1005 during fluid exchange. Due to the lower density of air relative to processing fluids, such orientation aids in the removal of air from the specimen chamber 1005 during fluid exchange, ensuring optimal surface contact for dyes and processing chemicals and preventing imaging distortion due to trapped air.

Methods of the invention may include single-chamber chemical processing, imaging, and wax embedding such that the tissue sample may be initially positioned within the chamber in a desired orientation for sectioning and/or imaging and left without further manipulation until removal of the wax-embedded sample for sectioning.

Chemical processing may include fixing, dehydrating, clearing, dying, and other steps known in the art and useful for both intact tissue imaging (e.g. fluorescent staining and imaging) and histological analysis (e.g., wax embedding and microtome sectioning). In certain embodiments, the tissue sample may be exposed to one or more stains, fixatives, dehydrants, and/or clearing agents within a single tissue chamber as described herein. In some instances, one or more of the above stains, fixatives, dehydrants, and/or clearing agents may be combined in a single solution. Suitable examples of chemical processing solutions and techniques are described in U.S. Pub. 2016/0003716 and U.S. Pub. 20160003715, the contents of each of which are incorporated herein by reference.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A container for holding a tissue sample, the container comprising a surface comprising a frangible area and a plurality of features configured to support a tissue sample and permit fluid flow between the tissue sample and the surface.

2. The container of claim 1, wherein the plurality of features comprise a material having a refractive index approximately equal to a refractive index of a fluid to be used in processing the tissue sample.

3. The container of claim 2, wherein the refractive index of the fluid to be used in processing the tissue sample is approximately equal to a refractive index of a structure of the tissue sample to be analyzed.

4. The container of claim 3, wherein the plurality of features comprise a material having a refractive index of about 1.5 to about 1.7.

5. The container of claim 4, wherein the plurality of features comprise a material having a refractive index of between about 1.53 and about 1.60.

6. The container of claim 1, wherein the plurality of features comprise a material that dissolves in the presence of an organic solvent.

7. The container of claim 6, wherein the organic solvent is a clearing solution.

8. The container of claim 1, comprising a porous compressible material configured to contact the tissue sample on a side of the tissue sample opposite the surface.

9. The container of claim 8, wherein the porous compressible material has a refractive index that is approximately equal to a refractive index of the tissue sample to be analyzed.

10. The container of claim 1, wherein at least a portion of the surface comprises a refractive index approximately equal to a refractive index of a fluid to be used in processing the tissue sample.

11. The container of claim 10, wherein the refractive index of the fluid to be used in processing the tissue sample is approximately equal to the refractive index of a structure of the tissue sample to be analyzed.

12. The container of claim 10, wherein the at least a portion of the surface comprises a refractive index of about 1.5 to about 1.7.

13. The container of claim 1, wherein the frangible area defines a perimeter.

14. The container of claim 13, wherein the frangible area comprises an area of thinned material relative to an area inside the perimeter.

15. The container of claim 1, further comprising one or more wax-retention members extending from the surface on a same side as the plurality of features.

16. The container of claim 1, further comprising one or more locating members extending from a side of the surface opposite the plurality of features.

17. The container of claim 1, wherein the surface at least partially defines a cavity for receiving the tissue sample.

18. The container of claim 17, comprising one or more fluid ports in fluid communication with the cavity for receiving the tissue sample and a space outside the cavity.

19. The container of claim 17, wherein the cavity for receiving tissue samples comprises a frangible area.

* * * * *